United States Patent
Ulrich et al.

(10) Patent No.: US 10,327,710 B2
(45) Date of Patent: Jun. 25, 2019

(54) AGE CALIBRATION FOR TISSUE OXIMETRY

(71) Applicant: Nonin Medical, Inc., Plymouth, MN (US)

(72) Inventors: Franz Ulrich, Minneapolis, MN (US); Aaron Alfred Lobbestael, Watertown, MN (US)

(73) Assignee: Nonin Medical, Inc., Plymouth, MN (US)

(*) Notice: Subject to any disclaimer, the term of this patent is extended or adjusted under 35 U.S.C. 154(b) by 72 days.

(21) Appl. No.: 14/352,285

(22) PCT Filed: Oct. 17, 2012

(86) PCT No.: PCT/US2012/060634
§ 371 (c)(1),
(2) Date: Apr. 16, 2014

(87) PCT Pub. No.: WO2013/059335
PCT Pub. Date: Apr. 25, 2013

(65) Prior Publication Data
US 2014/0243632 A1 Aug. 28, 2014

Related U.S. Application Data

(60) Provisional application No. 61/550,150, filed on Oct. 21, 2011.

(51) Int. Cl.
*A61B 5/1455* (2006.01)
*A61B 5/00* (2006.01)
*A61B 5/1495* (2006.01)

(52) U.S. Cl.
CPC .......... *A61B 5/7271* (2013.01); *A61B 5/1495* (2013.01); *A61B 5/14552* (2013.01);
(Continued)

(58) Field of Classification Search
None
See application file for complete search history.

(56) References Cited

U.S. PATENT DOCUMENTS

| | | |
|---|---|---|
| 2007/0060819 A1 | 3/2007 | Altshuler et al. |
| 2008/0221410 A1 | 9/2008 | Campbell et al. |
| 2010/0130840 A1 | 5/2010 | Isaacson |

FOREIGN PATENT DOCUMENTS

| | | |
|---|---|---|
| EP | 1738684 A1 | 1/2007 |
| WO | WO-0153805 A1 | 7/2001 |

(Continued)

OTHER PUBLICATIONS

"International Application Serial No. PCT/US2012/060634, International Search Report dated Aug. 29, 2013", 5 pgs.
(Continued)

*Primary Examiner* — Eric F Winakur
*Assistant Examiner* — Marjan Fardanesh
(74) *Attorney, Agent, or Firm* — Schwegman Lundberg & Woessner, P.A.

(57) ABSTRACT

A system (100) includes a sensor (12A/B/C), a processor (32), and an output module (38). The sensor can have at least one light emitter (16A) and at least one light detector (18A/B). The processor can be coupled to the sensor and have instructions configured to determine a calibration value using light attenuation corresponding to a light path through a tissue associated with a light emitter and a light detector of the sensor. The processor can be configured to calculate oxygen saturation in the tissue using a signal provided by the sensor. The output module can be coupled to the processor and configured to render a compensated oxygen saturation. The compensated oxygen saturation can be determined using the calibration value and the calculated oxygen saturation.

12 Claims, 4 Drawing Sheets

(52) U.S. Cl.
CPC .......... *A61B 5/14553* (2013.01); *A61B 5/742* (2013.01); *A61B 2560/0223* (2013.01)

(56) References Cited

FOREIGN PATENT DOCUMENTS

| WO | WO-2013059335 A2 | 4/2013 |
|---|---|---|
| WO | WO-2013059335 A3 | 4/2013 |

OTHER PUBLICATIONS

"International Application Serial No. PCT/US2012/060634, Written Opinion dated Aug. 29, 2013", 5 pgs.

Choi, Jeehyun, et al., "Noninvasive determination of the optical properties of adult brain: near-infrared spectroscopy apprach", Journal of Biomedical Optics, vol. 9 No. 1, (Jan./Feb. 2004), 221-229.

Hollis, Veronica S., "Non-Invasive Monitoring of Brain Tissue Temperature by Near-Infrared Spectroscopy", Retrieved from the Internet: <http://www.mpb.ucl.ac.uk/research/borl/homepages/veronica/thesis/abstract_ack_contents.pdf>, (Sep. 2002), 262 pgs.

Van Der Zee, Pieter, et al., "Optical properties of brain tissue", SPIE vol. 1888, (Jan. 18, 1993), 454-465.

"European Application Serial No. 12787569.8, Office Action dated Jul. 11, 2014", 2 pgs.

"European Application Serial No. 12787569.8, Response filed Jan. 21, 2015 to Office Action dated Jul. 11, 2014", 10 pgs.

"International Application Serial No. PCT/US2012/060634, International Preliminary Report on Patentability dated May 1, 2014", 7 pgs.

"European Application Serial No. 12787569.8, Response filed Oct. 25, 2016 to Communication Pursuant to Article 94(3) EPC dated Apr. 15, 2016", 5 pgs.

"Japanese Application Serial No. 2014-537180, Office Action dated Sep. 20, 2016", (w/ English Translation), 4 pgs.

European Application Serial No. 12787569.8, Communication Pursuant to Article 94(3) EPC dated Apr. 15, 2016, 3 pgs.

Japanese Application Serial No. 2014-537180, Response filed Dec. 20, 2016 to Office Action dated Sep. 20, 2016, w/ English translation, 11 pgs.

AGE CALIBRATION FOR TISSUE OXIMETRY

CLAIM OF PRIORITY

This patent application is a U.S. National Stage Application under 35 U.S.C. 371 from International Application No. PCT/US2012/060634, filed Oct. 17, 2012, published as WO 2013/059335, which claims the benefit of priority to U.S. Provisional Patent Application Ser. No. 61/550,150, entitled "AGE CALIBRATION FOR TISSUE OXIMETRY," filed on Oct. 21, 2011, which is hereby incorporated by reference herein in its entirety.

BACKGROUND

Optical properties of biological tissue can be used to determine oximetry. For example, a cerebral oximeter can be used to assess oxygen saturation of blood delivered to the brain in conjunction with certain types of surgical operations. A cerebral oximeter typically includes a sensor having light emitters and one or more light detectors operating in the near infrared spectrum where the human body is relatively transparent. To measure blood oxygen, the cerebral oximeter must separate the optical effects of tissue and blood.

During the first years of life, the optical properties of brain tissue undergo significant changes. To ensure accurate oximeter readings, users have been tasked with selecting a particular sensor unit tailored for a specific age. In another example, the user is required to manually enter patient age information to ensure accuracy.

Overview

The present subject matter addresses the problem of calibration by determining patient age based on optical attenuation properties of the biological tissue. In this manner, optical attenuation serves as a proxy for patient age. Optical, or light, attenuation is a measure of absorption properties and scattering properties of tissue.

The present inventors have recognized, among other things, that the problem of oximetry calibration can be addressed by determining light attenuation at the tissue site. The attenuation information can be used to determine oximetry calibration and ensure accurate measurements without requiring a user to select from different sensor units or to enter patient age information. In general, light attenuation correlates with the difference between light transmitted into the body and received out of the body by the cerebral oximeter.

Optical attenuation measurement data can be used to determine calibration of oxygen saturation. For example, in the absence of patient age information, light attenuation can be determined and used as a surrogate for age.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
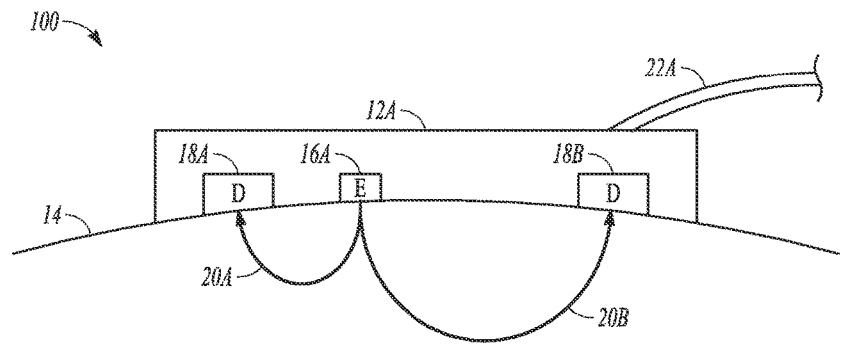
FIG. 1 illustrates a sensor at a tissue site, according to one example.

FIG. 1 illustrates system 100 including section view of sensor 12A at a site on a surface of tissue 14, according to one example. Sensor 12A is non-invasive and includes emitter 16A and detectors 18A and 18B. Link 22A couples sensor 12A with a monitor. Link 22A can include a fiber optic cable, an electrical cord, or a wireless link. The optical elements, emitter 16A and detectors 18A and 18B in this example, are disposed on a surface of sensor 12A. Sensor 12A, in one example, is tailored for near infrared spectroscopy (NIRS).

Emitter 16A can include a light emitting diode or other optical element and is configured to emit light into tissue 14. The emitted light can be at a wavelength that penetrates tissue. For cerebral oximetry, the light can be in the wavelength range of 660-940 nm.

Detectors 18A and 18B are positioned at fixed distances selected to provide measurements based on light paths having different depths of tissue penetration. In the figure, detector 18A is nearer to emitter 16A and thus provides a signal corresponding to a shallow penetration depth and detector 18B is farther from emitter 16A and thus provides a signal corresponding to a deeper penetration depth.

The penetration depth of the emitted photons (from emitter 16A) is proportional to the distance between emitter 16A and a receiving detector. In the case of a cerebral oximeter sensor, and according to the figure, detector 18A (located closer to emitter 16A) measures saturations within the scalp, whereas detector 18B (located further away) measures both cerebral as well as scalp saturations. By subtracting the measurements obtained from the detector 18A from the detector 18B, extracerebral contamination can be reduced.

Figure 2:
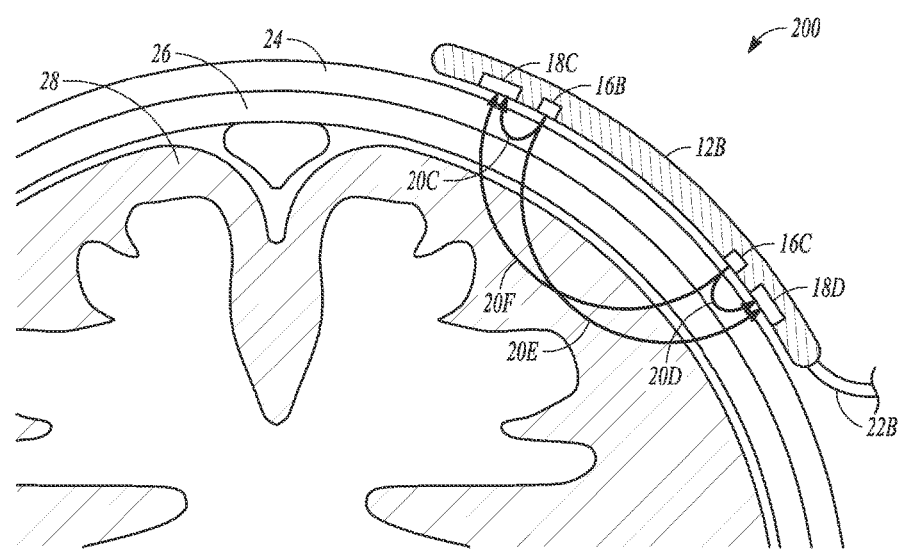
FIG. 2 illustrates a sensor at a cerebral tissue site, according to one example.

FIG. 2 illustrates system 200 including cerebral oximetry sensor 12B disposed near brain 28 at a site on tissue 24, according to one example. In the figure, sensor 12B includes emitter 16B, emitter 16C, detector 18C, and detector 18D. Link 22B couples sensor 12B with a monitor.

In the example illustrated, light emitted from emitter 16B passes through the tissue along relatively short path 20C (which includes scalp 26) and is detected at detector 18C. In similar manner, light emitted from emitter 16C passes through the tissue along relatively short path 20D (which also includes scalp 26) and is detected at detector 18D. Longer light paths 20E and 20F pass through brain 28 and correspond to greater depth of penetration, as shown in the figure.

Figure 3:
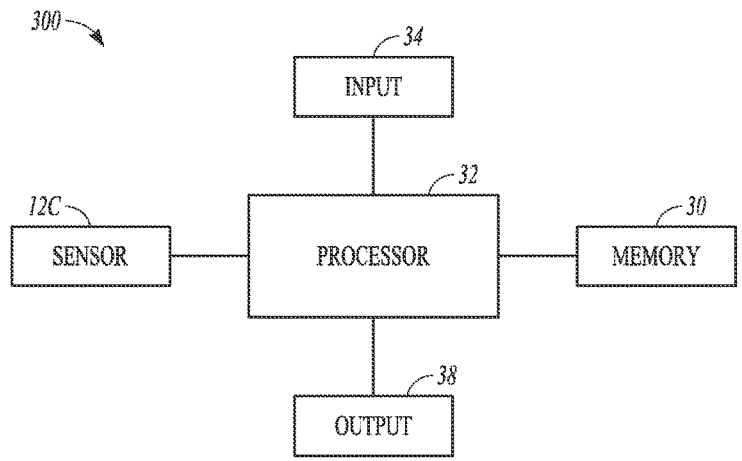
FIG. 3 illustrates a block diagram of a system, according to one example.

FIG. 3 illustrates block diagram of system 300, according to one example. System 300 includes sensor 12C, input module 34, processor 32, memory 30, and output module 38. Sensor 12C can include one or more emitters and one or more detectors and have a configuration consistent with that of sensor 12A and 12B described elsewhere in this document. Sensor 12C is coupled to processor 32.

Input module 34 is coupled to processor 32 and, in the example shown, can be configured to receive a user-entered input, such as a keyboard, a mouse, a touch screen, a microphone, a switch, or other input device. In addition, input module 34 can include an interface to allow data transfer with a communication network for purposes of receiving (and sending) data. In one example, input module 34 is omitted and system 300 is functional without user-entered data.

Memory 30 is coupled to processor 32 and can include a storage device configured to store data such as measured data, calculated data, and calibration data. In one example, memory 30 is configured to store instructions for execution by processor 32 to implement an algorithm as described herein.

Output 38 is coupled to processor 32 and, in various examples, can include a display, a speaker, a storage device, and a network connection.

Figure 4:
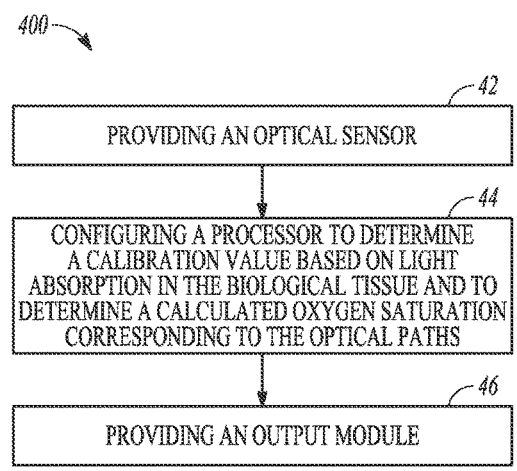
FIG. 4 illustrates a method performed according to one example.

FIG. 4 illustrates method 400 according to one example of the present subject matter. At 42, method 400 includes providing an optical sensor. The optical sensor can include a cerebral oximeter sensor, a tissue oximetry sensor, or other component having an emitter and a detector.

At 44, method 400 includes configuring a processor to determine a calibration value based on light attenuation in the biological tissue. In addition, method 400 includes configuring a processor to determine a calculated oxygen saturation corresponding to the optical paths in the tissue.

At 46, method 400 includes providing an output module. In one example, the output module is coupled to the processor, as shown in FIG. 3.

Figure 5:
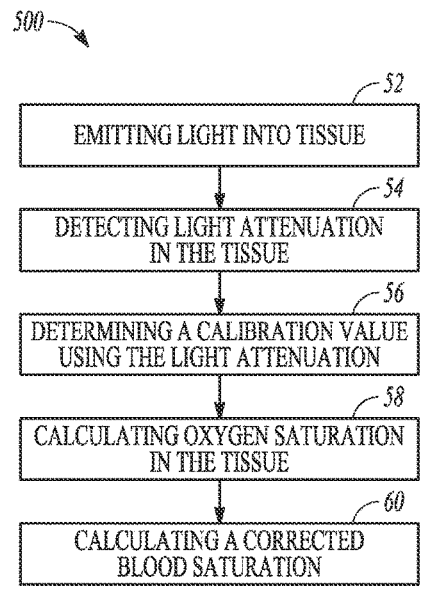
FIG. 5 illustrates a method performed according to one example.

FIG. 5 illustrates method 500, according to one example. At 52, method 500 includes emitting light into tissue. The light can have one wavelength in the near infrared region or the light can have a plurality of wavelengths. The light can pass through the tissue via a number of light paths and the light paths can have varying depths of penetration in the tissue. At 54, method 500 includes detecting light attenuation in the tissue. Light attenuation can be determined using the intensity of light emitted into the tissue and the intensity of light received from the tissue.

The light attenuation can be determined by a signal from a light detector as described herein. At 56, method 500 includes determining a calibration value using the light attenuation. The calibration value is indicative of tissue maturation. Tissue maturation refers to development of the tissue. In one example, the chronological age of the patient is commensurate with the tissue maturation. At 58, method 500 includes calculating oxygen saturation in the tissue. At 60, method 500 includes calculating a corrected (or compensated) oxygen saturation using the calculated oxygen saturation and the calibration value.

A cerebral oximeter can include two detectors having different spacing from an emitter element. An example is shown in FIG. 1. Multiple detectors can be helpful for isolating the light attenuation measurement to the brain tissue. The emitter-to-detector spacing of the detector located closer to the emitter is chosen so that the majority of the light path penetrates the forehead and the skull of the patient and does not penetrate the gray matter. This light path is referred to as the short path.

The spacing of the further detector is chosen such that the light path penetrates the gray matter, as well as the forehead and skull, and is referred to as the long path.

Light attenuation can be expressed as the difference between the light measurements of the short path detector and the long path detector.

In certain circumstances, this configuration of optical elements does not fully isolate the brain tissue light attenuation since any difference in the optical properties of the skull and forehead in the regions beneath the two detectors will erroneously contribute to the light attenuation measurement.

To mitigate this problem, a second emitter can be used, as shown in the example of FIG. 2. In this example, light attenuation can be measured along two paths, with each path corresponding to an emitter. The optical element spacing is selected such that the long and short paths are reversed for each emitter's measurement. In this example, an average light attenuation can be calculated using a difference between a first long path and a short path and a difference between a second long path and a short path.

This reversal causes the skull and forehead optical differences associated with each detector to be canceled out, thereby yielding a more accurate light attenuation measurement of the brain tissue.

Another consideration for measuring light attenuation is error caused by ambient light. Room light or natural light is readily transmitted from the surface of the skin to the detectors. To mitigate the effects of ambient light, the ambient light can be measured while the emitters are off and used to cancel the ambient light while the emitters are on. In addition, suitable low noise amplification and signal processing can be used to reduce artifacts from noise and power line hum.

Figure 6:
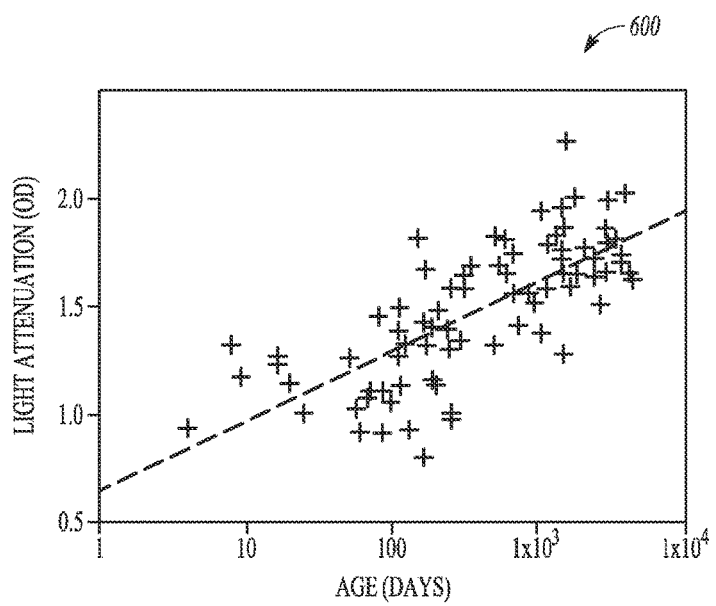
FIG. 6 illustrates a graph indicating light attenuation and age.

FIG. 6 illustrates graph 600 indicating a relationship between light attenuation and age. A study of 100 pediatric subjects can yield data as shown in graph 600. The light attenuation (ordinate) is measured in units of optical density and age is shown on the abscissa. Optical density uses a logarithmic scale with 1 representing a factor 10 light attenuation and 2 representing a factor 100.

The light attenuation Pearson correlation coefficient with age is 0.68. To reduce the effect of oxygen saturation on light attenuation, a wavelength of light close to the isobestic point in the spectral response of oxygenated and deoxygenated hemoglobin is used.

As light attenuation changes, the path length through the tissue from emitter to detector changes. If the light attenuation change is the same for all wavelengths used by the emitters, then the blood oxygen calculation is unaffected. If the change is wavelength dependent, then the path length can be adjusted accordingly. More explicitly, light attenuation of a chromophore given by the Beer-Lambert law can be expressed as:

$$LA = \varepsilon * L * C$$

where LA=light attenuation, ε=chromophore molar absorptivity, L=path length, and C=chromophore concentration.

To compensate for path length changes, the relationship can be modified to give:

$$LA = (1 + \delta_s * LA) * \varepsilon * L * C$$

where $\delta_s$=sensitivity of path length to light attenuation.

To evaluate the effectiveness of this correction, data on pediatric subjects of various ages can be collected using invasive measurement of the cerebral oxygen saturation using arterial and jugular bulb blood draws. Using Beer-Lambert techniques on four wavelengths to separate the optical response of blood and tissue on the subjects and comparing the calculated oxygen saturation to the invasively measured oxygen saturation yields data as shown in FIG. 7.

Figure 7:
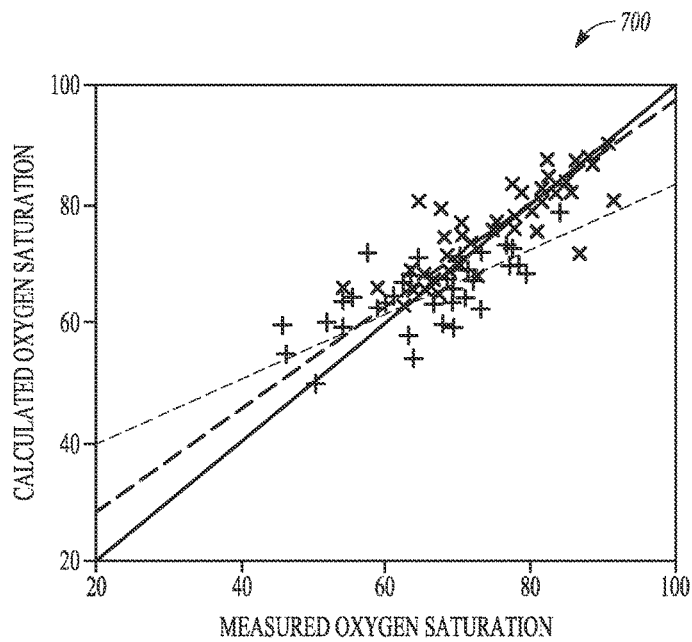
FIGS. 7 and 8 illustrate graphs indicating calculated and measured oxygen saturation.

FIG. 7 illustrates graph 700 indicating calculated oxygen saturation and measured oxygen saturation. In the graph, + symbols represent an age under 9 months (line indicated with light dash characters) and x symbols represent an age greater than 9 months (line indicated with heavy dash characters). The data illustrates calculations made without path length correction (that is, without the benefit of age-related compensation).

Figure 8:
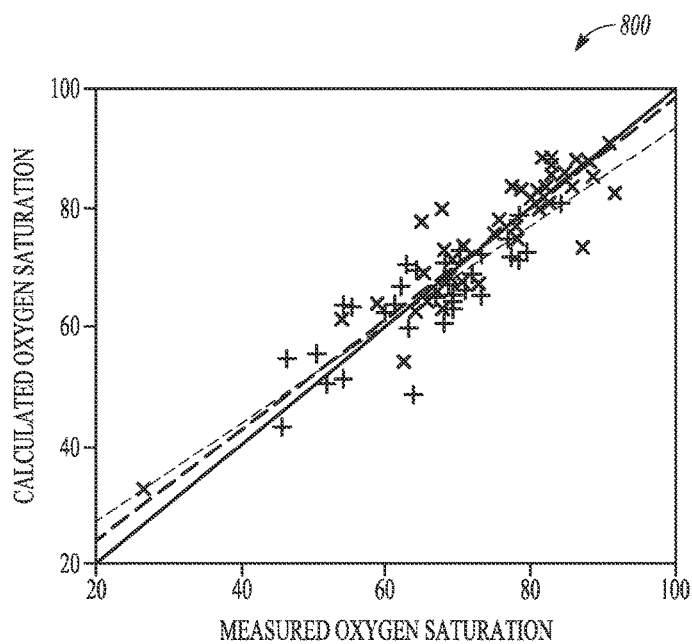

Light attenuation data can be used to alter the path length in order to compensate for patient age. FIG. 8 illustrates graph 800 indicating calculated and measured oxygen saturation based on calibration using light attenuation. In the graph, + symbols represent an age under 9 months (line indicated with light dash characters) and x symbols represent an age greater than 9 months (line indicated with heavy dash characters). The data illustrates calculations made with path length correction (that is, with the benefit of age-related compensation).

The path length sensitivity can be determined by making a best fit to the data. The light attenuation compensation results in a more consistent slope between younger and older subjects and better accuracy (smaller standard deviation from ideal). Example results are summarized in Table 1 below.

TABLE 1

| | Without Light Attenuation Compensation for Age | With Light Attenuation Compensation for Age |
|---|---|---|
| Subject age less than 9 months (blue) | Slope = 0.62, $\sigma$ = 7.2 | Slope = 0.84, $\sigma$ = 6.0 |
| Subject age greater than 9 months (red) | Slope = 0.93, $\sigma$ = 4.9 | Slope = 0.94, $\sigma$ = 4.7 |

In one example of the present subject matter, a single light path through the tissue is used to measure both tissue oximetry and to determine age related calibration. The single light path can be defined by one light emitter and one light detector.

In one example, two light paths (a pair of light paths) are used to measure both tissue oximetry and to determine age related calibration. The pair of light paths can be defined by one light detector and two light emitters. The pair of light paths can be defined by one light emitter and two light detectors. The pair of light paths can be configured so that one path passes through the tissue at a shallow penetration depth and one path passes through the tissue at a deep penetration depth. Age calibration can be determined by one or two of the two light paths through the tissue. In a similar manner, tissue oximetry can be determined by one or two of the two light paths through the tissue. A path having a shallow penetration depth can be called a short path and a path having a deep penetration depth can be called a long path.

In one example, more than two light paths are used to measure both tissue oximetry and to determine age related calibration. The plurality of light paths can be defined by one or more light detectors and one or more light emitters. The plurality of light paths can be configured so that at least one path passes through the tissue at a shallow penetration depth and at least one path passes through the tissue at a deep penetration depth. Age calibration can be determined by one or more of the plurality of light paths through the tissue. In a similar manner, tissue oximetry can be determined by one or more of the plurality of light paths through the tissue.

The sensor is configured to measure light attenuation between the long/deep and short/shallow signal paths to eliminate blood measurements in the shallow tissue. The optical signals can be calibrated against $S_{av}O_2$ to create an algorithm to calculate regional cerebral oxygen saturation ($rSO_2$). Accuracy can be assessed using the root mean square error (ARMS). Orthogonal regression can be used for assessing the linear relationship between $S_{av}O_2$ and $rSO_2$.

To examine the effectiveness of this correction, light attenuation data from study subjects can be calibrated to the $S_{av}O_2$ data by making a regression fit to a four wavelength Beer-Lambert formulation with and without path length correction. Without correction, the accuracy was ARMS=6.0 and representative data are plotted in FIG. 7. Note the difference between subjects less than and greater than 9 months of age. When correction based on light attenuation was implemented, the accuracy improved to ARMS=5.3. Representative data are plotted in FIG. 8. Note the slope consistency for subjects less than and greater than 9 months of age.

Dynamic compensation allows one sensor size and calibration to measure neonatal, pediatric and child subjects with a weight less than 40 kg without the need to enter age and/or weight into the system.

An example of the present subject matter can improve the accuracy from ARMS=6.0 to ARMS=5.3 by accounting for brain development. The overall accuracy of ARMS=5.3 is noted for subjects with a wide variety of age, skin color, bilirubin concentration, hemoglobin concentration and arterial saturation.

Various Notes & Examples

Example 1 includes a system having a sensor, a processor, and an output module. The sensor can have at least one light emitter and at least two light detectors. The processor can be coupled to the sensor and have instructions configured to determine a calibration value using light attenuation corresponding to a light path through a tissue associated with a light emitter and a light detector of the sensor. The processor can be configured to determine calculated oxygen saturation in the tissue using a signal provided by the sensor. The output module can be coupled to the processor and configured to render calculated (or compensated) oxygen saturation. The compensated oxygen saturation can be determined using the calibration value and the calculated oxygen saturation. Rendering of the compensated oxygen saturation by the output module can include displaying a value or data using a user interface, printing a result, or transmitting (wirelessly or by a wired link) the result to a remote device.

In Example 2, the subject matter of Example 1 can optionally include the processor configured to determine an age of the tissue using the light attenuation.

In Example 3, the subject matter of one or any combination of Examples 1-2 and can optionally include an input module coupled to the processor, the input module configured to receive a user input.

In Example 4, the subject matter of one or any combination of Examples 1-3 can optionally include wherein the at least one light emitter and the at least two light detectors are arranged to provide a plurality of optical paths including at least one short path and at least one long path.

In Example 5, the subject matter of one or any combination of Examples 1-4 and can optionally include wherein the sensor is configured to emit light through cerebral tissue.

In Example 6, the subject matter of one or any combination of Examples 1-5 and can optionally include wherein the processor is configured to control a wavelength of light emitted by the at least one emitter.

In Example 7, the subject matter includes a method. The method can include providing an optical sensor configured to detect light in biological tissue corresponding to a plurality of optical paths. The method can include configuring a processor to determine a calibration value based on light attenuation in the biological tissue and to determine a calculated saturation corresponding to the optical paths. The method can include providing an output module configured to render a compensated oxygen saturation using the calculated oxygen saturation and the calibration value.

Example 8 can include the subject matter of Example 7 and can optionally include wherein the calibration value corresponds to an age of the biological tissue.

Example 9 can include the subject matter of one or any combination of Examples 7-8 and can optionally include wherein configuring the processor includes providing instructions to cause the processor to determine oxygen saturation based on light emitted at a plurality of wavelengths.

Example 10 can include the subject matter of one or any combination of Examples 7-9 and can optionally include wherein configuring the processor includes providing instructions to determine light attenuation in the biological tissue at a plurality of wavelength.

Example 11 can include the subject matter of one or any combination of Examples 7-10 and can optionally include wherein providing the output module includes configuring a display or configuring a memory.

Example 12 can include subject matter such as a method comprising emitting light into tissue, detecting light attenuation in the tissue, determining a calibration value using the light attenuation, calculating oxygen saturation in the tissue, and determining a compensated oxygen saturation using the calculated oxygen saturation and the calibration value.

Example 13 can include the subject matter of Example 12 and optionally include wherein detecting light attenuation includes determining intensity of light emitted into the tissue and determining intensity of light received from the tissue.

Example 14 can include the subject matter of one or any combination of Examples 12-13 and optionally include wherein determining the calibration value includes determining an age of the tissue.

Example 15 can include the subject matter of one or any combination of Examples 12-14 and optionally include wherein emitting light includes emitting light at a plurality of wavelengths.

Example 16 can include the subject matter of one or any combination of Examples 12-15 and optionally include wherein emitting light includes emitting light on a plurality of paths in the tissue.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with The claimed invention is:

1. A system comprising:
   a sensor having at least one light emitter configured to emit light at a first intensity;
   a first light detector and a second light detector, wherein the at least one light emitter and the first and second light detectors are arranged relative to one another to provide a plurality of optical paths including at least one short path and at least one long path, the short path resulting from placing the first light detector at a first distance from the at least one emitter, the long path resulting from placing the second light detector at a second distance from the at least one emitter, the second distance being greater than the first distance;
   a processor coupled to the sensor and the first and second light detectors, the processor having executable instructions, the instructions configured to determine an age calibration value based on light attenuation using a difference between an absolute value of a second intensity of the light received at the first light detector and an absolute value of a third intensity of the light received at the second light detector, and the instructions further configured to calculate oxygen saturation of blood in the tissue using a signal provided by the first and second light detectors; and
   an output module coupled to the processor and configured to render a compensated oxygen saturation, the compensated oxygen saturation determined by the processor based on the calculated oxygen saturation of blood and an optical path having a length that is altered by the age calibration value.

2. The system of claim 1 further including an input nodule coupled to the processor, the input module configured to receive a user input.

3. The system of claim 1 wherein the at least one emitter is configured to emit light at a wavelength configured to pass through cerebral tissue.

4. The system of claim 1 wherein the processor is configured to control a wavelength of light emitted by the at least one emitter.

5. A method comprising:
   providing an optical sensor including a light emitter to emit light at a first intensity in biological tissue;
   providing a first light detector configured to detect the light corresponding to a short optical path in the biological tissue, the short optical path resulting from placement of the first light detector at a first distance from the light emitter;
   providing a second light detector configured to detect the light corresponding to a long optical path in the biological tissue, the long optical path resulting from placement of the second light detector at a second distance from the light emitter, the second distance being greater than the first distance;
   coupling configuring a processor to the optical sensor and the first and second light detectors, the processor configured to receive output from and first and second light detectors and execute instructions;
   determining an age calibration value using the processor and based on light attenuation in the biological tissue using a difference between an absolute value of a second intensity of the light received at the first light detector and an absolute value of a third intensity of the light received at the second light detector;
   determining a calculated oxygen saturation using the processor and a signal provided by the first and second light detectors;
   determining a compensated oxygen saturation using the calculated oxygen saturation of blood and an optical path having a length that is altered by the age calibration value; and
   providing an output module configured to render the determined compensated oxygen saturation.

6. The method of claim 5 wherein configuring the processor includes providing instructions to cause the processor to determine oxygen saturation based on light emitted at a plurality of wavelengths.

7. The method of claim 5 further comprising:
   providing instructions to determine light attenuation in the biological tissue at a plurality of wavelengths.

8. The method of claim 5 wherein providing the output module configured to render the compensated oxygen saturation includes configuring a display or configuring a memory.

9. A method comprising:
   emitting light at a first intensity into tissue using an emitter of an optical sensor;
   detecting a second intensity of the light received at a first light detector corresponding to a short path through the tissue, the short path resulting from placement of the first light detector at a first distance from the emitter;
   detecting a third intensity of the light received at a second light detector corresponding to a long path through the tissue, the long path resulting from placement of the second light detector at a second distance from the emitter, the second distance being greater than the first distance;
   determining an age calibration value based on light attenuation using a difference between an absolute value of the second intensity and an absolute value of the third intensity;
   calculating oxygen saturation in the tissue using a signal provided by the first and second light detectors; and
   calculating a compensated oxygen saturation using the calculated oxygen saturation and an optical path having a length that is altered by the age calibration value.

10. The method of claim 9 wherein the light attenuation is determined based on intensity of light emitted into the tissue and intensity of light received from the tissue.

11. The method of claim 9 wherein emitting light includes emitting light at a plurality of wavelengths.

12. The method of claim 9 wherein emitting light includes emitting light on a plurality of paths in the tissue.

* * * * *

UNITED STATES PATENT AND TRADEMARK OFFICE
CERTIFICATE OF CORRECTION

PATENT NO. : 10,327,710 B2  
APPLICATION NO. : 14/352285  
DATED : June 25, 2019  
INVENTOR(S) : Ulrich et al.

Page 1 of 1

It is certified that error appears in the above-identified patent and that said Letters Patent is hereby corrected as shown below:

On the Title Page

On page 2, in Column 1, under "Other Publications", Line 4, delete "apprach"," and insert --approach",-- therefor In the Claims In Column 9, Line 34, in Claim 2, delete "nodule" and insert --module-- therefor In Column 9, Line 57, in Claim 5, after "coupling", delete "configuring"

Signed and Sealed this  
Eleventh Day of May, 2021

Drew Hirshfeld  
*Performing the Functions and Duties of the  
Under Secretary of Commerce for Intellectual Property and  
Director of the United States Patent and Trademark Office*